(12) United States Patent
Burnette et al.

(10) Patent No.: US 10,241,113 B2
(45) Date of Patent: Mar. 26, 2019

(54) CD28 EXPRESSION DURING LENALIDOMIDE IMMUNE MODULATION

(71) Applicant: H. LEE MOFFITT CANCER CENTER AND RESEARCH INSTITUTE, INC., Tampa, FL (US)

(72) Inventors: Pearlie Burnette, Tampa, FL (US); Jessica M. McDaniel, Etna, OH (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/434,542

(22) PCT Filed: Oct. 10, 2013

(86) PCT No.: PCT/US2013/064295
§ 371 (c)(1),
(2) Date: Apr. 9, 2015

(87) PCT Pub. No.: WO2014/059117
PCT Pub. Date: Apr. 17, 2014

(65) Prior Publication Data
US 2015/0276741 A1    Oct. 1, 2015

Related U.S. Application Data

(60) Provisional application No. 61/712,132, filed on Oct. 10, 2012.

(51) Int. Cl.
*G01N 33/574* (2006.01)
*A61K 31/454* (2006.01)
*G01N 33/569* (2006.01)

(52) U.S. Cl.
CPC ......... *G01N 33/574* (2013.01); *A61K 31/454* (2013.01); *G01N 33/56972* (2013.01); *G01N 2333/70521* (2013.01); *G01N 2800/52* (2013.01)

(58) Field of Classification Search
None
See application file for complete search history.

(56) References Cited

FOREIGN PATENT DOCUMENTS

WO    2012129514 A1    9/2012

OTHER PUBLICATIONS

Maki et al., Journal of Gastroenterology and Hepatology, 2004, 19:1348-1356.*
Melchert et al., Curr Opin Hematol, 2007, 14:123-127.*
McDaniel et al., Blood, Nov. 18, 2011, 118(21), abstract No. 1117.*
Lenschow et al., Annu. Rev. Immunol. 1996, 14:233-58.*
Zeng et al., the Abstract of Zhongguo Shiyan Xueyexue Zazhi, 2008, 16(5):1082-1085 (one page).*
Ebert et al., PLoS Medicine, 2008, 5(2): e35, pp. 0312-0322.*
McDaniel, Lenalidomide targets the T-cell co-stimulatory pathway to mediate immune modulation, Dissertation, University of South Florida, pub. date: Jan. 2012 (Year: 2012).*
Akbar AN, et al. Memory T cell homeostasis and senescence during aging. Curr Opin Immunol 2005 17(5):480-5.
Angers S, et al. Molecular architecture and assembly of the DDB1-CUL4A ubiquitin ligase machinery. Nature 2006 443(7111):590-3.
Infante, et al. Lenalidomide in combination with gemcitabine in patients with untreated metastatic carcinoma of the pancreas: A Sarah Cannon Research Institute phase II trial. ASCO annual meeting, Journal of Clinical Oncology 2011 29.
Bachmaier K, et al. Negative regulation of lymphocyte activation and autoimmunity by the molecular adaptor Cbl-b. Nature 2000 403(6766):211-6.
Brown RD, et al. Dendritic cells from patients with myeloma are numerically normal but functionally defective as they fail to up-regulate CD80 (B7-1) expression after huCD40LT stimulation because of inhibition by transforming growth factor-beta1 and interleukin-10. Blood 2001 98(10):2992-8.
Carter JS, et al. A prospective clinical trial of lenalidomide with topotecan in women with advanced epithelial ovarian carcinoma. Int J Clin Oncol 2011 16(6):666-70.
Cefai D, et al. CD28 receptor endocytosis is targeted by mutations that disrupt phosphatidylinositol 3-kinase binding and costimulation. J Immunol 1998 160(5):2223-30.
Chanan-Khan A, et al. Tumor flare reaction associated with lenalidomide treatment in patients with chronic lymphocytic leukemia predicts clinical response. Cancer 2011 117(10)2127-35.
Chiang et al. Cbl-b regulates the CD28 dependence of T-cell activation. Nature 2000 403(6766):216-20.
Czesnikiewicz-Guzik M, et al. T cell subset-specific susceptibility to aging. Clin Immunol 2008 127(1):107-18.
Drake CG, Jaffee E, Pardoll DM. Mechanisms of immune evasion by tumors. Adv Immunol 2006 90:51-81.
Dredge K, et al. Protective antitumor immunity induced by a costimulatory thalidomide analog in conjunction with whole tumor cell vaccination is mediated by increased Th1-type immunity. J Immunol 2002 168(10):4914-9.
Effros RB. Loss of CD28 expression on T lymphocytes: a marker of replicative senescence. Dev Comp Immunol 1997 21(6):471-8.

(Continued)

*Primary Examiner* — Hong Sang
(74) *Attorney, Agent, or Firm* — Meunier Carlin & Curfman LLC

(57) ABSTRACT

Disclosed are compositions and methods for predicting responsiveness of a subject to treatment with lenalidomide (LEN) by assaying a sample from the subject for surface expression of CD28 on T-cells. Also provided is a method of treating a subject for cancer that involves assaying a sample from the subject for surface expression of CD28 on T-cells and then treating them with LEN if they do not have reduced CD28 surface expression on the T-cells. Also provided is a method for promoting responsiveness of a subject to LEN by administering to the subject a composition that promotes expression of CD28 on the surface of T-cells.

6 Claims, 12 Drawing Sheets

(56) References Cited

OTHER PUBLICATIONS

Eisen T, et al. Results of a multicenter, randomized, double-blind phase 2/3 study of lenalidomide in the treatment of pretreated relapsed or refractory metastatic malignant melanoma. Cancer 2010 116(1):146-54.

Epling-Burnette, PK, Han, Y, Rajadhyaksha, AM, Mailloux, AW, McDaniel, J. Novel Predictor of Lenalidomide Response in non-del5q MDS Reveals Linkage to Molecular Mechanism: First Characterization of T-cell Function in Cereblon Homozygous Deficient Mice. Presentation at 2013American Society of Hematology (ASH) Meeting, New Orleans, LA, Dec. 7, 2013.

Fowler NH MP, Kwak L, Hagemeister F, Fanale M, Fayad L, Pro B, Samaniego F. Lenalidomide and rituximab for untreated indolent non-Hodgkin's lymphoma [abstract]. J Clin Oncol 2009 27(15s):8548.

Galustian C, Meyer B, Labarthe MC, et al. The anti-cancer agents lenalidomide and pomalidomide inhibit the proliferation and function of T regulatory cells. Cancer Immunol Immunother 2009 58(7):1033-45.

Giannopoulos K, Schmitt M, Wlasiuk P, et al. The high frequency of T regulatory cells in patients with B-cell chronic lymphocytic leukemia is diminished through treatment with thalidomide. Leukemia 2008 22(1):222-4.

Gimmi CD, Freeman GJ, Gribben JG, et al. B-cell surface antigen B7 provides a costimulatory signal that induces T cells to proliferate and secrete interleukin 2. Proc Natl Acad Sci U S A 1991 88(15):6575-9.

Glaspy J, Atkins MB, Richards JM, et al. Results of a multicenter, randomized, double-blind, dose-evaluating phase 2/3 study of lenalidomide in the treatment of metastatic malignant melanoma. Cancer Nov. 15, 2009;115(22):5228-36.

Görgün G, Calabrese E, Soydan E, Hideshima T, Perrone G, Bandi M, Cirstea D, Santo L, Hu Y, Tai YT, Nahar S, Mimura N, Fabre C, Raje N, Munshi N, Richardson P, Anderson KC. Immunomodulatory effects of lenalidomide and pomalidomide on interaction of tumor and bone marrow accessory cells in multiple myeloma. Blood. 2010 116(17):3227-37.

Gruber T, Hermann-Kleiter N, Hinterleitner R, et al. PKC-theta modulates the strength of T cell responses by targeting Cbl-b for ubiquitination and degradation. Sci Signal 2009;2(76):ra30.

Harding FA, McArthur JG, Gross JA, Raulet DH, Allison JP. CD28-mediated signalling co-stimulates murine T cells and prevents induction of anergy in T-cell clones. Nature Apr. 16, 1992;356(6370):607-9.

Haslett PA, Corral LG, Albert M, Kaplan G. Thalidomide costimulates primary human T lymphocytes, preferentially inducing proliferation, cytokine production, and cytotoxic responses in the CD8+ subset. J Exp Med Jun. 1, 1998;187(11)1885-92.

Hideshima T, Raje N, Richardson PG, Anderson KC. A review of lenalidomide in combination with dexamethasone for the treatment of multiple myeloma. Ther Clin Risk Manag. 2008 4(1):129-36.

Hwu WJ, Knight RD, Patnana M, et al. Phase I safety study of lenalidomide and dacarbazine in patients with metastatic melanoma previously untreated with systemic chemotherapy. Melanoma Res Dec. 2010;20(6):501-6.

Ito T, Ando H, Suzuki T, et al. Identification of a primary target of thalidomide teratogenicity. Science Mar. 12, 2010;327(5971):1345-50.

Kane LP, Lin J, Weiss A. It's all Rel-ative: NF-kappaB and CD28 costimulation of T-cell activation. Trends Immunol Aug. 2002;23(8):413-20.

Kotla V, Goel S, Nischal S, Heuck C, Vivek K, Das B, Verma A. Mechanism of action of lenalidomide in hematological malignancies. J Hematol Oncol. 2009 2:36.

Lee BN, Gao H, Cohen EN, et al. Treatment with lenalidomide modulates T-cell immunophenotype and cytokine production in patients with chronic lymphocytic leukemia. Cancer Sep. 1, 2011;117(17):3999-4008.

Linsley PS, Greene JL, Brady W, Bajorath J, Ledbetter JA, Peach R. Human B7-1 (CD80) and B7-2 (CD86) bind with similar avidities but distinct kinetics to CD28 and CTLA-4 receptors. Immunity Dec. 1994;1(9):793-801.

List A, Kurtin S, Roe DJ, et al. Efficacy of lenalidomide in myelodysplastic syndromes. N Engl J Med Feb. 10, 2005;352(6):549-57.

List AF LJ, Melchert M, Saba H, Lush R, Yu J, Chen N, Schmidt M, Knight R. Abstract: Two-stage pharmacokinetic and efficacy study of Lenalidomide alone or combined with recombinant erythropoietin (EPO) in lower risk MDS EPO-failures [PK-002]. 49th Annual American Society of Hematology Meeting 2007;110(4626).

Lopez-Girona A, Mendy D, Ito T, et al. Cereblon is a direct protein target for immunomodulatory and antiproliferative activities of lenalidomide and pomalidomide. Leukemia May 3, 2012.

McDaniel JM, Zou JX, Fulp W, Chen DT, List AF, Epling-Burnette PK. Reversal of T-cell tolerance in myelodysplastic syndrome through lenalidomide immune modulation. Leukemia Jun. 2012;26(6):1425-9.

Noonan K, Rudraraju L, Ferguson A, et al. Lenalidomide-induced immunomodulation in multiple myeloma: impact on vaccines and antitumor responses. Clin Cancer Res Mar. 1, 2012;18(5):1426-34.

Neuber B, Herth I, Tolliver C, Schoenland S, Hegenbart U, Hose D, Witzens-Harig M, Ho AD, Goldschmidt H, Klein B, Hundemer M. Lenalidomide enhances antigen-specific activity and decreases CD45RA expression of T cells from patients with multiple myeloma. Immunol. 2011 187(2):1047-56.

Petrylak DP, Resto-Garces, K., Tibyan, M., Mobile, S.G. A phase I open-label study using lenalidomide and docetaxel in castration-resistant prostate cancer. ASCO annual meeting, Journal of Clinical Oncology 2009.

Pfaffl MW. A new mathematical model for relative quantification in real-time RT-PCR. Nucleic Acids Res May 1, 2001;29(9):e45.

Rajadhyaksha AM, RA S, Kishinevsky S, et al. Behavioral characterization of cereblon forebrain-specific conditional null mice: a model for human non-syndromic intellectual disability. Behav Brain Res Jan. 15, 2012;226(2):428-34.

Raza A, Reeves JA, Feldman EJ, et al. Phase 2 study of lenalidomide in transfusion-dependent, low-risk, and intermediate-1 risk myelodysplastic syndromes with karyotypes other than deletion 5q. Blood Jan. 1, 2008;111(1):86-93.

Sallusto F, Lenig D, Forster R, Lipp M, Lanzavecchia A. Two subsets of memory T lymphocytes with distinct homing potentials and effector functions. Nature Oct. 14, 1999;401(6754):708-12.

Salmond RJ, Filby A, Qureshi I, Caserta S, Zamoyska R. T-cell receptor proximal signaling via the Src-family kinases, Lck and Fyn, influences T-cell activation, differentiation, and tolerance. Immunol Rev Mar. 2009;228(1):9-22.

Sanchez-Lockhart M, Mahn E, Graf B, et al. Cutting edge: CD28-mediated transcriptional and posttranscriptional regulation of IL-2 expression are controlled through different signaling pathways. J Immunol Dec. 15, 2004;173(12):7120-4.

Schmidt D, Goronzy JJ, Weyand CM. CD4+ CD7-CD28-T cells are expanded in rheumatoid arthritis and are characterized by autoreactivity. J Clin Invest May 1, 1996;97(9):2027-37.

Schmitz ML. Activation of T cells: releasing the brakes by proteolytic elimination of Cbl-b. Sci Signal 2009;2(76):pe38.

Shahinian A, Pfeffer K, Lee KP, et al. Differential T cell costimulatory requirements in CD28-deficient mice. Science Jul. 30, 1993;261(5121):609-12.

Smith MA, Wright G, Wu J, et al. Positive regulatory domain I (PRDM1) and IRF8/PU.1 counter-regulate MHC class II transactivator (CIITA) expression during dendritic cell maturation. J Biol Chem Mar. 11, 2011;286(10):7893-904.

Stein PH, Fraser JD, Weiss A. The cytoplasmic domain of CD28 is both necessary and sufficient for costimulation of interleukin-2 secretion and association with phosphatidylinositol 3'-kinase. Mol Cell Biol May 1994;14(5):3392-402.

Venuprasad K. Cbl-b and itch: key regulators of peripheral T-cell tolerance. Cancer Res Apr. 15, 2010;70(8):3009-12.

Viola a, Schroeder S, Sakakibara Y, Lanzavecchia A. T lymphocyte costimulation mediated by reorganization of membrane microdomains. Science Jan. 29, 1999;283(5402):680-2.

(56) References Cited

OTHER PUBLICATIONS

Wu L, Adams M, Carter T, et al. lenalidomide enhances natural killer cell and monocyte-mediated antibody-dependent cellular cytotoxicity of rituximab-treated CD20+ tumor cells. Clin Cancer Res Jul. 15, 2008;14(14):4650-7.

Wu L, Parton A, Lu L, Adams M, Schafer P, Bartlett JB. Lenalidomide enhances antibody-dependent cellular cytotoxicity of solid tumor cells in vitro: influence of host immune and tumor markers. Cancer Immunol Immunother Jan. 2011;60(1):61-73.

Zhang MM, Chan JK, Husain A, Guo HY, Teng NN. Safety and efficacy of lenalidomide (Revlimid) in recurrent ovarian and primary peritoneal carcinoma. Gynecol Oncol Apr. 2007;105(1):194-8.

International Search Report and Written Opinion issued in international application No. PCT/US2013/064295 dated Jan. 2, 2014.

* cited by examiner

CD28 EXPRESSION DURING LENALIDOMIDE IMMUNE MODULATION

CROSS REFERENCE TO RELATED APPLICATIONS

This application is a national stage entry of PCT Patent Application No. PCT/US13/64295, filed Oct. 10, 2013, which claims the benefit of U.S. Provisional Application No. 61/712,132 filed Oct. 10, 2012, both of which are hereby incorporated herein by reference in their entirety.

STATEMENT REGARDING FEDERALLY SPONSORED RESEARCH OR DEVELOPMENT

This invention was made with Government support under Grant No. CA129952 awarded by the National Institutes of Health (NIH). The Government has certain rights in the invention.

BACKGROUND

Lenalidomide (LEN) is a second-generation thalidomide analogue with potent immune-modulating activity with FDA approval in myelodysplastic syndrome (MDS) and multiple myeloma (MM). Although LEN is approved for the treatment of MDS and MM, there are subsets of patients that are naturally resistant to the drug.

SUMMARY

Disclosed are compositions and methods for predicting responsiveness of a subject to treatment with lenalidomide (LEN). The method comprises assaying a sample from the subject for surface expression of CD28 on T-cells. Detection of CD28 expression on the surface of T cells in the sample from the subject is an indication that the subject will be responsive to treatment with LEN. Reduce surface expression of CD28 on the T-cells of the subject is an indication that the subject will be unresponsive or have diminished responsiveness to LEN treatment.

For example, the T-cells can be $CD8^+$ T-cells. Therefore, in some embodiments, detection of CD28 surface expression on less than 40%, 45%, 50%, 55%, 60%, 65%, 70%, 75%, or 80% of the $CD8^+$ T-cells is an indication that the subject will be unresponsive or have diminished responsiveness to LEN treatment. Therefore, the method can further comprise treating the subject with lenalidomide if at least 40%, 45%, 50%, 55%, or 60% of the $CD8^+$ T-cells of the subject have detectable CD28 surface expression.

The T-cells can also be $CD4^+$ T-cells. Therefore, in some embodiments, detection of CD28 surface expression on less than 95%, 96%, 97%, 98%, 99%, or 100% of the $CD4^+$ T-cells is an indication that the subject will be unresponsive or have diminished responsiveness to LEN treatment. Therefore, the method can further comprise treating the subject with lenalidomide if at least 90%, 95%, 96%, 97%, 98%, or 99% of the $CD4^+$ T-cells of the subject have detectable CD28 surface expression.

In some embodiments, the subject is being treated for a hematological cancer or disorder. For example, in some cases, the subject is being treated for myelodysplastic syndrome (MDS), multiple myeloma (MM), B-Chronic Lymphocytic Leukemia (B-CLL) or Non-Hodgkin's Lymphoma (NHL). In some embodiments, the subject is being treated for a cancer, such as a solid tumor. For example, in some cases, the subject is being treated for metastatic melanoma, castration resistant prostate cancer, pancreatic adenocarcinoma, or ovarian cancer.

Therefore, also disclosed is a method for treating a subject with a hematological cancer or disorder. The method can first comprise assaying a sample from the subject for surface expression of CD28 on $CD4^+$ and/or $CD8^+$ T-cells. The method can then comprise treating the subject with lenalidomide if at least 40%, 45%, 50%, 55%, or 60% of the $CD8^+$ T-cells, at least 90%, 95%, 96%, 97%, 98%, or 99% of the $CD4^+$ T-cells, or a combination thereof, have detectable CD28 surface expression.

Also disclosed is a method for treating a subject with a solid tumor that involves first assaying a sample from the subject for surface expression of CD28 on $CD4^+$ and/or $CD8^+$ T-cells. The method can then comprise treating the subject with lenalidomide alone if at least 40%, 45%, 50%, 55%, or 60% of the $CD8^+$ T-cells, at least 90%, 95%, 96%, 97%, 98%, or 99% of the $CD4^+$ T-cells, or a combination thereof, have detectable CD28 surface expression. Alternatively, the method can involve treating the subject with a combination of lenalidomide and a chemotherapeutic if less than 40%, 45%, 50%, 55%, or 60% of the $CD8^+$ T-cells, less than 90%, 95%, 96%, 97%, 98%, or 99% of the $CD4^+$ T-cells, or a combination thereof, have detectable CD28 surface expression.

Also provided is a method for promoting responsiveness of a subject to LEN. The method comprises administering to the subject a composition that promotes expression of CD28 on the surface of T-cells.

The details of one or more embodiments of the invention are set forth in the accompanying drawings and the description below. Other features, objects, and advantages of the invention will be apparent from the description and drawings, and from the claims.

DESCRIPTION OF DRAWINGS

In FIGS. 1A(i) to 1A(vi) T-cells purified from healthy donor PBMCs were stimulated in the presence of increasing concentrations of anti-CD3 in the presence of 10 μM lenalidomide (Len) or vehicle control (DMSO). A subset of cells was stimulated with both anti-$CD3^+CD28$ as a positive control. Proliferation and IL-2 production was measured in culture supernatant of cells stimulated with increasing concentrations of purified T-cells treated with 5 μg/ml anti-CD3 and increasing concentrations of Len (i, ii, iii, v, vi). Proliferation was measured by S-phase transition as indicated by incorporation of BrdU by flow-cytometry in $CD4^+$ (FIG. 1A(i)) and $CD8^+$ (FIG. 1A(ii)) T-cells. In FIGS. 1A(iii) to 1A(v), IL-2 was measured via ELISA. In FIG. 1A(iv), IL-2 was measured by ELISA after treatment with DMSO or LEN in the presence of anti-$CD3^+$ anti-CD28 (1.0 μg/ml). In FIG. 1A(vi), IL-2 mRNA expression was examined using RT-qPCR after 18 hours of increasing concentrations of anti-CD3 stimulation. In FIG. 1B, Murine T-cells were isolated from the spleen of B57BL6 mice and treated with increasing doses of anti-CD3 and either DMSO or LEN. Proliferation by BrdU incorporation (FIGS. 1B(i) to 1B(ii)) and IL-2 (FIGS. 1B(iii) to 1B(iv)) via ELISA were determined—2-way non-parametric ANOVA. *=p<0.05, ***=p<0.001.

FIG. 2 shows that CD28-specific transcription factor binding is induced after LEN treatment. FIG. 2A is a schematic of transcription factor binding sites on the IL-2 promoter. Arrows indicate forward and reverse primers used in Chromatin Immunoprecipitation (ChIP) to evaluate pCREB binding to the CD28-Response Element of the IL-2 promoter.

FIG. 3C shows CD28 mRNA expression measured after 18 hours of anti-CD3 stimulation after LEN and DMSO treatment. P values in all instances are not significant.

FIG. 4 shows knockdown of CD28 expression abrogates LEN activity in T-cells. CD28$^+$ T-cells were sorted from healthy donors and transfected with either non-target (control siRNA) or CD28 siRNA. T-cells were then stimulated with either 1.0 or 10 μg/ml anti-CD3 and 2.0 μg/ml anti-CD28 for 48 and 72 hours in the presence of 10 μM Lenalidomide or vehicle control (DMSO).

FIG. 6 shows that non-responder MDS patients have higher levels of Terminal Effector Memory (TEM) CD8$^+$ T-cells and lower levels of CD28$^+$ T-cells. The proportion of naïve, central memory (CM), effector memory (EM), and terminal effector memory (TEM) T-cells with CD4 and CD8 expression from MDS patients treated in vivo with LEN was determined using flow cytometry.

DETAILED DESCRIPTION

Figure 1A:
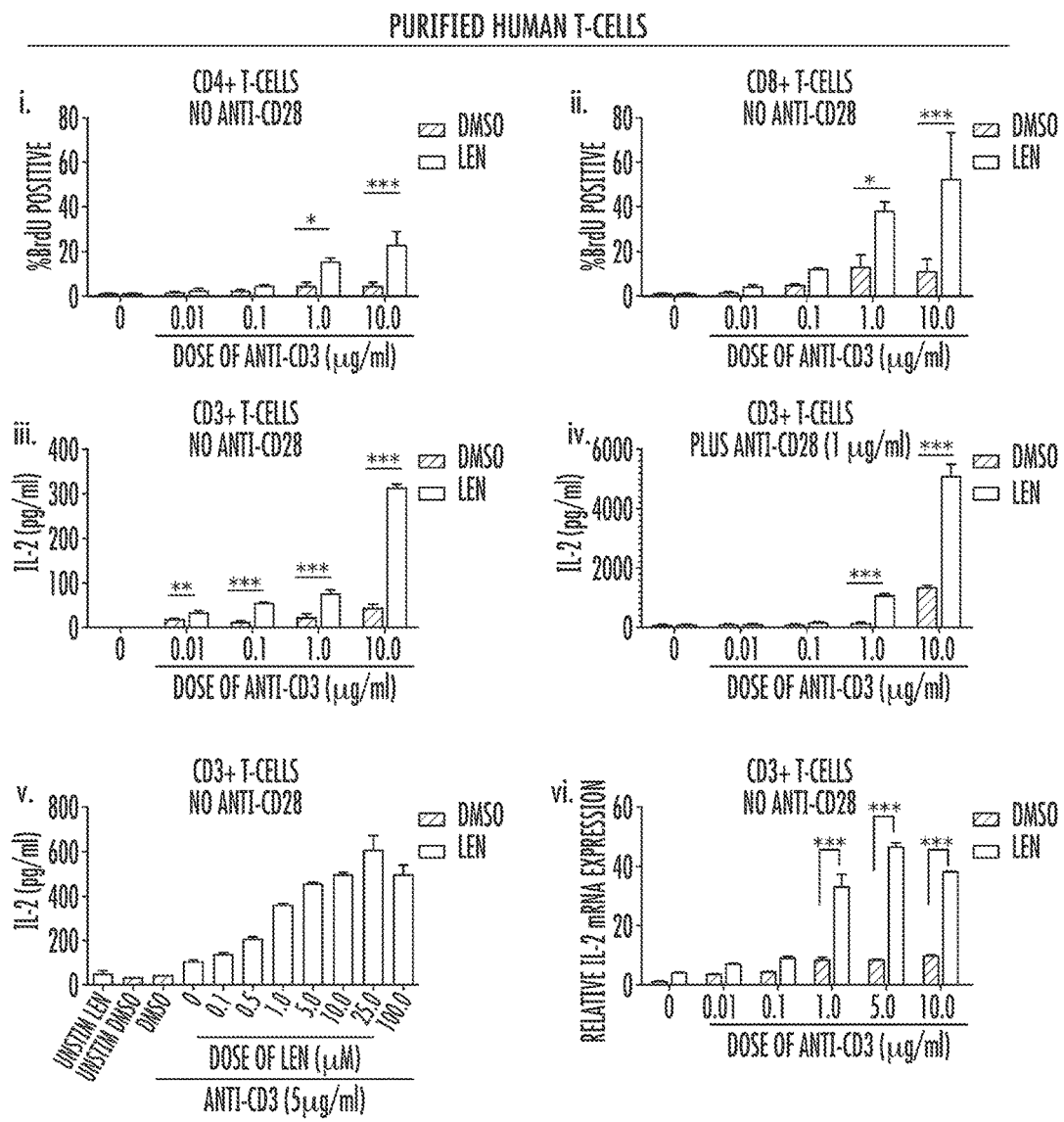
FIGS. 1A to 1B show that lenalidomide increases IL-2 production in the absence of CD28 external co-ligation in human but not murine T-cells.

CD28 is a member of the B7 family of T-cell co-stimulatory molecules that binds to CD80/CD86 (B7-1/B7-2) expressed on APCs (Linsley P S, et al. Immunity 1994 1(9):793-801). When the T-cell receptor (TCR) CD3 complex is activated, engagement of the CD28 co-stimulatory pathway is essential for the induction of interleukin-2 (IL-2) gene expression and for the prevention of tolerance/anergy within a TCR-activated T-cell population (Harding F A, et al. Nature 1992 356(6370):607-9). CD28 is a transmembrane protein that contains two immunotyrosine activation motifs (ITAMs) within the cytoplasmic tail (Salmond R J, et al. Immunol Rev 2009 228(1):9-22). Receptor-ligand interaction induces CD28 homo-dimerization, phosphorylation by src-family kinases lck and fyn, and the activation of downstream signaling mediators including Vav1, Grb2, phosphoinositide 3-kinase (PI3K) and extracellular signal-regulated kinases (ERK) 1/2 (ERK1/2) (Salmond R J, et al. Immunol Rev 2009 228(1):9-22; Stein P H, et al. Mol Cell Biol 1994 14(5):3392-402; Sanchez-Lockhart M, et al. J Immunol 2004 173(12):7120-4). Absence of CD28 co-stimulation has been implicated in tumor immune evasion and is an important barrier to the success of tumor vaccine therapy, usually occurring due to B71/2 down-regulation or loss of CD28 expression (Drake C G, et al. Adv Immunol 2006 90:51-81).

Stimulation of the TCR complex is insufficient to induce an immune response (Gimmi C D, et al. Proc Natl Acad Sci USA 1991 88(15):6575-9). The necessity of CD28 for IL-2 production has been illustrated using CD28 homozygous deficient (−/−) mice, which lack the ability to induce IL-2 in response to antigen stimulation (Shahinian A, et al. Science 1993 261(5121):609-12). CD28 is inherently expressed on both CD4$^+$ and CD8$^+$ T-cell subsets. Aging of the immune system in humans, however, is associated with the accumulation of CD28-deficient (CD28$^-$, CD28$^{null}$) T-cells, altering T-cell homeostasis and reducing pathogen and vaccine immune responses (Akbar A N, et al. Curr Opin Immunol 2005 17(5):480-5). CD28 receptor down-regulation results from either chronic TNF-α exposure or repeated TCR engagement indicative of robust in vivo proliferative history (Effros R B. Dev Comp Immunol 1997 21(6):471-8).

Manipulation of the CD28 pathway is an important goal to improve the success of cancer immunotherapy. Lenalidomide (LEN) is a second-generation thalidomide analogue with potent immune-modulating activity with FDA approval in MDS and multiple myeloma (MM). Although known to augment CD28 signaling, the mechanism of LEN action was poorly understood. The presence of an interstitial deletion on chromosome 5q [del(5q)] enhances apoptotic responses of myeloid clones in MDS, and improves hematologic response rates (List A, et al. N Engl J Med 2005 352(6): 549-57). Approval for LEN in non-del(5q) MDS was issued based on erythroid improvement in a subset of patients (Raza A, et al. Blood 2008 111(1):86-93).

It has been unclear if LEN mediates hematologic improvement through immune modulation in MDS, multiple myeloma or in lymphomas where it is investigational. Increased TNF-α production in chronic lymphocytic leukemia (CLL) (Lee B N, et al. Cancer 2011 17(17):3999-4008), as well as other Th-1 type cytokines is thought to contribute to tumor flare response (TFR), an adverse side effect of LEN closely associated with hematologic improvement (Chanan-Khan A, et al. Cancer 2011 117(10):2127-35). In CLL, LEN potentially works through enhancing reactivation of tumor-specific T-cells, and an increase in NK-mediated cytotoxicity is also implicated in the success of rituximab and LEN combination therapy (Fowler, et al. J Clin Oncol 2009 27(15s):8548). T-cells from MDS patients are inherently non-responsive/anergic to stimulation, and secrete less T-cell activating cytokines (McDaniel J M, et al. Leukemia 2012 26(6):1425-9). Lymphoid aggregates increase in the bone marrow of MDS patients that improve hematologically to LEN, implicating reactivation of tumor-specific T-cells in the response (List A, et al. N Engl J Med 2005 352(6):549-57). Patients with erythroid improvement have an increase in T-cell proliferation and an increase in IL-2 and Th1 cytokine production after TCR activation (McDaniel J M, et al. Leukemia 2012 26(6):1425-9). Normalization of the naïve:memory T-cell ratio in responders is also consistent with immune reactivation against the myeloid clone.

As disclosed herein, CD28 expression is critical for T-cell co-stimulation. Absence of this receptor or its ligand (B7-1/2) on antigen presenting cells (APCs) contributes to immune evasion and is a barrier to the success of cancer immunotherapy. Manipulation of the CD28 pathway is therefore an important goal of cancer therapy. LEN, a thalidomide analog, has immunomodulatory activity in multiple myeloma and MDS and expands tumor-reactive T-cells. LEN augments co-stimulation by increasing IL-2 production and mRNA expression in the absence of external CD28 ligation. LEN increases the binding of a CD28-specific transcription factor pCREB to the IL-2 promoter when activation is delivered only through the TCR indicating that CD28-selective signaling is induced. An increase in CD28 surface expression, with similar mRNA and total protein expression after LEN treatment suggests that the drug may alter receptor trafficking Comparisons of LEN-induced T-cell responses in sorted $CD28^+CD8^+$ and $CD28^-CD8^+$ T-cells, and in cells treated with siRNA CD28 knockdown compared to control illustrates the role of this molecule in LEN-induced proliferation and IL-2 production. The pre-treatment percentage of $CD28^+$ cells (as a continuous variable) was correlated to hematologic response in MDS patients treated with LEN. Non-responders (NR) had more $CD4^+$ (p=0.02) and $CD8^+$ (p=0.03) $CD28^-$ T-cells within the total T-cell compartment and within memory cells compared to responders (R). CD28 receptor expression is therefore required for LEN-induced T-cell co-stimulation and pretreatment immunophenotyping may be exploited as a predictive biomarker in immunotherapy regimens.

The cancer of the disclosed methods can be any cell in a subject undergoing unregulated growth, invasion, or metastasis. In some aspects, the cancer can be any neoplasm or tumor for which LEN is currently used. The cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed methods may be used to determine whether to co-administer LEN with another chemotherapeutic. The majority of chemotherapeutic drugs can be divided in to: alkylating agents, antimetabolites, anthracyclines, plant alkaloids, topoisomerase inhibitors, monoclonal antibodies, and other antitumour agents. All of these drugs affect cell division or DNA synthesis. Some newer agents don't directly interfere with DNA. These include the new tyrosine kinase inhibitor imatinib mesylate (Gleevec® or Glivec®), which directly targets a molecular abnormality in certain types of cancer (chronic myelogenous leukemia, gastrointestinal stromal tumors). In addition, some drugs can be used which modulate tumor cell behavior without directly attacking those cells. Hormone treatments fall into this category of adjuvant therapies.

CD28 surface expression on T-cells can be detected using standard immunodetection methods, such as immuneflorescent imaging or flow cytometry.

The compositions disclosed can be used therapeutically in combination with a pharmaceutically acceptable carrier. The carrier would naturally be selected to minimize any degradation of the active ingredient and to minimize any adverse side effects in the subject, as would be well known to one of skill in the art. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, and anesthetics.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained. See, e.g., U.S. Pat. No. 3,610,795, which is incorporated by reference herein.

The compositions disclosed herein may be administered prophylactically, e.g., to patients or subjects who are at risk for cancer. Thus, the method can further comprise identifying a subject at risk for cancer prior to administration of the herein disclosed compositions.

The exact amount of lenalidomide required can vary from subject to subject, depending on the species, age, weight and general condition of the subject, the severity of the disorder being treated, and mode of administration. Effective dosages and schedules for administering lenalidomide may be determined empirically, and making such determinations is within the skill in the art. The dosage can be adjusted by the individual physician in the event of any counterindications.

Dosage can vary, and can be administered in one or more dose administrations daily, for one or several days. Guidance can be found in the literature for appropriate dosages for given classes of pharmaceutical products. A typical daily dosage of the antibody used alone might range from about 1 µg/kg to up to 100 mg/kg of body weight or more per day, depending on the factors mentioned above. In some embodiments, lenalidomide is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "sample from a subject" refers to a tissue, organ, cell, or body fluid from a subject. In some embodiments, the body fluid is blood.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

EXAMPLES

Example 1

Materials and Methods

T-Cell Isolation and Activation.

Peripheral blood from buffy coats of healthy donors was obtained from the Southwest Florida Blood Services, St. Petersburg, Fla., for use as controls and for the purification of T-cells. T-cells were isolated from the buffy coats using RosetteSep® Human CD3+ T-cell Enrichment Cocktail (StemCell Technologies, Vancouver, BC Canada) according to the manufacturer's protocol. B57BL6 mice were maintained at an animal facility in accordance with the University of South Florida Committee on Animal Care. All mice were adult age 8-12 weeks, obtained from The Jackson Laboratory, and maintained in a pathogen-free environment at Moffitt Cancer Center. Mouse-specific antibodies for T-cell activation were purchased from eBioscience (San Diego, Calif.) and human-specific antibodies were purchased from BD Biosciences (San Jose, Calif. USA). To activate the T-cell receptor (TCR), T-cells were stimulated with plate-bound anti-CD3 antibody (1 µg/ml or indicated concentration) coated onto flat-bottomed polystyrene tissue culture plates overnight at 4° C. Purified T-cells ($1 \times 10^6$/ml) were added to the coated 96-well plates in a 200 µl volume for 48 hours at 37° C. In some instances, 1.0 µg/ml anti-CD28 was added for co-stimulation.

Stimulation followed by measurement of CD28 surface expression was performed using anti-CD3 (10 µg/ml) alone or anti-CD3 (10 µg/ml) plus anti-CD28 (10 µg/ml) coupled 4.5 micron polystyrene polybeads (Polysciences, Inc, Warrington, Pa. USA). $1 \times 10^5$ beads were added to $2 \times 10^5$ cells in u-bottom 96-well plates, as previously described (Viola A, et al. Science 1999 283(5402):680-2). Cells were collected at 72 hours and 5 days, and CD28 surface expression was measured via flow cytometry on LSRII flow cytometer (BD Biosciences, San Jose, Calif. USA).

Preparation of LEN for In Vitro Studies.

Lenalidomide (Revlimid®) was provided by Celgene Corporation (Warren, N.J.). The drug was weighed and dissolved at the time of use in dimethyl sulfoxide (DMSO) and diluted 1:1000 in culture media to a final concentration of 10 µM (or indicated concentration) because storage of stock solutions at –20° C. resulted in variable loss in activity. An equal volume of DMSO was used as a vehicle control.

T-Cell Proliferation.

Proliferation was determined after in vitro activation by bromodeoxyuridine (BrdU) incorporation (BrdU flow kit, BD Biosciences, San Diego, Calif. USA). 10µl of BrdU was added during the last 45 min of T-cell stimulation. BrdU pulsed T-cells were harvested and stained with anti-CD4-PE and anti-CD8-PE-Cy-5 (BD Pharmingen, San Jose, Calif. USA). The cells were then fixed and permeabilized with BD Cytofix/Cytoperm buffer and incubated with DNase for 1 hour at 37° C. Cells were stained with anti-BrdU-FITC antibody before flow cytometry analysis on an LSRII flow cytometer (BD Biosciences, San Jose, Calif. USA). The percentage of BrdU positive cells from each population was analyzed using Flow-Jo Software (TreeStar Inc, Ashland, Oreg. USA.).

Cell Sorting.

T-cells were purified from healthy donor buffy coats as previously described, and were stained with 4',6-diamidino-2-phenylindole (DAPI) for viability, anti-CD8-APC-Cy7, CD4-PerCP-Cy5.5, and CD28-FITC antibodies (BD Pharmingen, San Jose, Calif.). Cells were then sorted into $CD8^+CD28^+$, $CD8^+CD28^-$ populations via FACS Aria Cell Sorter (BD Pharmingen, San Jose, Calif.).

siRNA Transfection and ELISA.

For siRNA knockdown (KD), T-cells were transfected with siCD28 or control siRNA (Santa Cruz Biotechnology, Inc, Santa Cruz, Calif. USA) using Amaxa Nucleofection technology (Lonza, Basel, Switzerland). $10 \times 10^6$ purified T-cells were mixed with either control or CD28 siRNA in 100 µl Human T-cell nucleofection solution, nucleofected, and then placed in Lymphocye Media (Lonza Basel, Switzerland). Cells were rested 24 hours before being stimulated with either plate bound anti-CD3, or anti-CD3+CD28, antibodies in the presence or absence of LEN. CD28 surface expression was measured via flow cytometry at 48 and 72 hours after stimulation, at the same time supernatant was collected for ELISA analysis. Supernatant from stimulation experiments was frozen at –80° C. for analysis via Human IL-2 ELISA kit (eBioscience, San Diego, Calif. USA).

RT-qPCR.

Total RNA was extracted from purified T-cells using the RNeasy Mini Kit (Qiagen, Chatsworth, Calif. USA). Reverse transcription was performed using the iScript cDNA synthesis kit (Biorad, Inc. Hercules, Calif. USA) in accordance with the manufacturer's suggestions. Relative target gene expression was measured by qRT-PCR using 18S rRNA expression as a reference gene. Expression levels of target mRNA and 18S rRNA were evaluated with Taqman Probes obtained from Applied Biosystems (Carlsbad, Calif.). All samples for both target genes (IL-2 or CD28) and 18S rRNA were measured in triplicate. Relative mRNA expression level for each sample was calculated using the $\Delta\Delta Ct$ method (Pfaffl M W. Nucleic Acids Res 2001 May 1; 29(9):e45).

Chromatin Immunoprecipitation (ChIP).

Cells were isolated, fixed, lysed, and sonicated before chromatin-immunoprecipitation, as previously described (Smith M A, et al. J Biol Chem 2011 Mar. 11; 286(10): 7893-904). Briefly, after stimulation and drug treatment, primary T-cells were treated with 1% formaldehyde for 10 min for cross-linking, followed by cell and nuclear lysis (50 mM Tris, pH 8.1, 10 mM EDTA, 1% SDS, 0.5 mM PMSF) and shearing. Chromatin was immunoprecipitated using 5 µg anti-phospho-CREB antibody (Millipore, Temecula, Calif. USA) and protein A/G beads (Santa Cruz Biotechnology Inc., Santa Cruz, Calif. USA). Immunoprecipitated chromatin was collected and washed sequentially with TSE buffer (20 mM Tris, pH 8.1, 50 mM NaCl, 2 mM EDTA, 0.1% SDS, 1.0% Triton X-100) and LiCl buffer (100 mM Tris, pH 8.1, 50 mM LiCl, 1% Nonidet P-40, 1% sodium deoxycholic acid, 1 mM EDTA). DNA was then eluted from the beads with 50 mM $NaHCO_3$ containing 1% SDS and cross-linking reversed at 65° C. overnight followed by proteinase K treatment. DNA was then purified via QIAquick PCR purification kit (Qiagen, Germantown, Md. USA). For each sample, 4 µl DNA was amplified and measured using Sybr Green (Bio-Rad, Inc., Hercules, Calif. USA). Primers used to amplify the pCREB binding site-180 upstream of the transcription start site were: forward: 5'-AGAAGGCGTTAATTGCATGAATT-3' (SEQ ID NO:1) and reverse: 5'-TCCTCTTCTGATGACTCTTTGGA-3' (SEQ ID NO:2).

MDS Patient Samples.

MDS patients (n=100) were consented at H. Lee Moffitt Cancer Center in Tampa, Fla. to participate in a peripheral blood collection protocol approved by the University of South Florida Institutional Review Board from 2004-2009. All patients signed University of South Florida Institutional Review Board approved informed consents for the collection of 40 ml of peripheral blood in heparin tubes. Samples were obtained from each patient at various times from 2004-2009 for immune monitoring studies and all cells were frozen in liquid nitrogen. Twenty-one of these patients had samples that were collected within 4 weeks prior to LEN treatment. LEN was administered at a dose of 10 mg for 21 out of a 28-day cycle for four cycles. All patients were evaluated for hematologic response after 16 weeks according to 2006 International Working Group Criteria (IWG). Hematologic response was reported previously within a larger cohort of MDS patients (List A F, et al. 49th Annual American Society of Hematology Meeting 2007 110(4626)).

Analysis of T-Cell Naïve and Memory Populations.

Naïve and memory CD4 and CD8 T-cell subtypes in MDS patients and healthy donors were detected after surface staining with anti-CD3-PE-Cy7, anti-CD8-PerCP-Cy5.5, anti-CD45RA-FITC, anti-CD27-APC, anti-CD28-PE, and DAPI (all from BD Biosciences, San Jose, Calif. USA). Naïve and memory T-cell populations have distinguishing immunophenotypes (McDaniel J M, et al. Leukemia 2012 26(6):1425-9; Sallusto F, et al. Nature 1999 401(6754):708-12). Briefly, the memory phenotype populations are characterized as naïve ($CD45R^+/CD27^+$), central memory ($CD45RA^-/CD27^+$), effector memory ($CD27^-/CD45RA^-$), and terminal effector memory ($CD45RA^+$ $VCD27^-$). Samples were run on an LSRII flow cytometer (BD Pharmingen) and populations were analyzed by FlowJo Software (Tree Star Inc., Ashland, Oreg. USA).

Results

LEN Induces Robust Interleukin-2 (IL-2) Production in the Absence of CD28 Co-Stimulation.

LEN has been shown to enhance proliferation and IL-2 expression/secretion in T-cells (Haslett P A, et al. J Exp Med 1998 187(11):1885-92) and based on biochemical and knockout mouse studies, the expression of IL-2 is completely dependent upon CD28 activation (Stein P H, et al. Mol Cell Biol 1994 14(5):3392-402; Gimmi C D, et al. Proc Natl Acad Sci USA 1991 88(15):6575-9; Shahinian A, et al. Science 1993 261(5121):609-12). To determine if LEN increases IL-2 in the absence of APCs or without the addition of anti-CD28 antibody, primary purified $CD3^+$ T-cells were isolated to greater than 95% purity from human donor peripheral blood and mouse spleens (FIGS. 1A and B, respectively). Increasing concentrations of species-specific anti-CD3 antibody in the presence of LEN or an equal volume of drug vehicle control (DMSO) (FIG. 1A) were used for stimulation in the presence or absence of anti-CD28 antibody. The TCR stimulus induced fewer proliferating cells (% BrdU positive) and failed to induce IL-2 in human T-cells (FIG. 1A, i-iii) compared to those treated with anti-CD28 co-stimulation (FIG. 1A, iv) illustrating a role for co-stimulation. LEN increased the production of IL-2 and stimulated more cells to proliferate in a dose dependent fashion compared to control cells treated with DMSO. LEN treatment was also able to increase, by an average of 6-fold, IL-2 production in T-cells that received both the TCR signal through anti-CD3 antibody stimulation plus anti-CD28 ($p<0.001$, FIG. 1A, iv) co-stimulation, showing that LEN augments the signal initiated by CD28. Purified human T-cells were then stimulated with a fixed dose (5 µg/ml) of anti-CD3 alone with increasing concentrations of LEN to demonstrate the dose-dependency of IL-2 production (FIG. 1A, v). In addition to protein secretion, it was found that LEN enhances IL-2 mRNA expression. A dose-dependent increase in IL-2 mRNA was present in cells treated with anti-CD3 alone without anti-CD28 after 18 hours compared to DMSO-treated cells, indicating that LEN transcriptionally activates the IL-2 gene (FIG. 1A, vi).

Figure 1B:
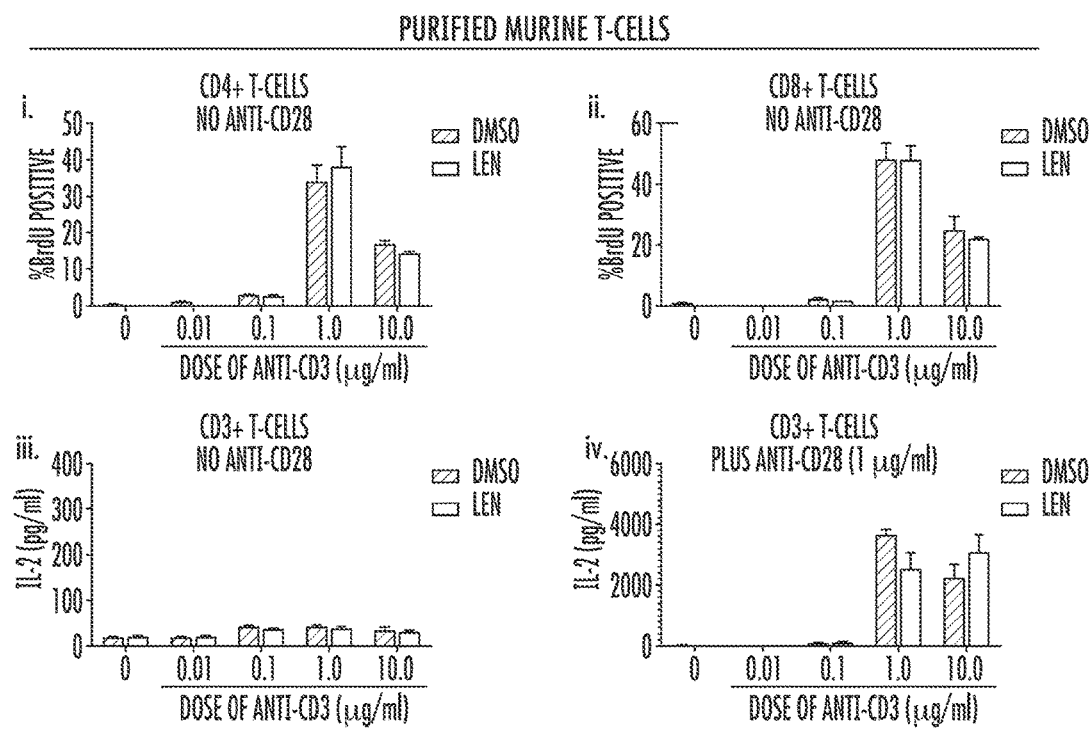

To investigate the role of CD28 in LEN's ability to induce IL-2, CD28 deficient mice could be used. Although a few murine studies have been reported testing IMiD efficacy (Dredge K, et al. J Immunol 2002 168(10):4914-9; Galustian C, et al. Cancer Immunol Immunother 2009 58(7):1033-45), species-specific differences are well-known to occur with these agents. Thalidomide shows teratogenic activity only in humans, rabbits, chickens and zebrafish, but not in rodents (Ito T, et al. Science 2010 327(5971):1345-50). Therefore, LEN's co-stimulatory function was investigated in murine T-cells with regard to proliferation (FIG. 1B, i-ii) and IL-2 (FIG. 1B, iii-iv) production. LEN treatment failed to induce IL-2 production in TCR-stimulated T-cells although the TCR signal plus anti-CD28 ($p<0.001$, FIG. 1A, iv) co-stimulation resulted in more than 2000 pg/ml of IL-2. Moreover, LEN failed to intensify the anti-CD28 signaling response in muring T-cells (FIG. 1B, iii-iv). This data indicates that there is a species-specific immune-modulating effect induced by LEN and therefore mechanistic studies focused solely on human T-cells.

LEN Augments a CD28-Specific Transcription Factor.

Figure 2A:
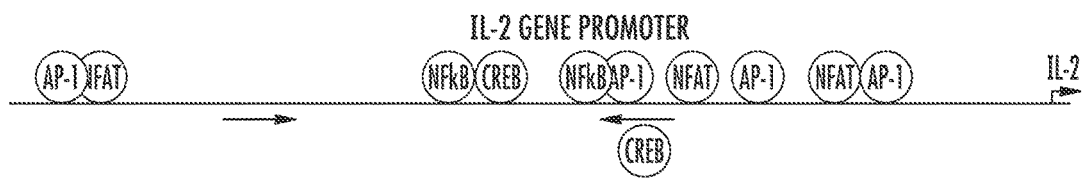
Figure 2B:
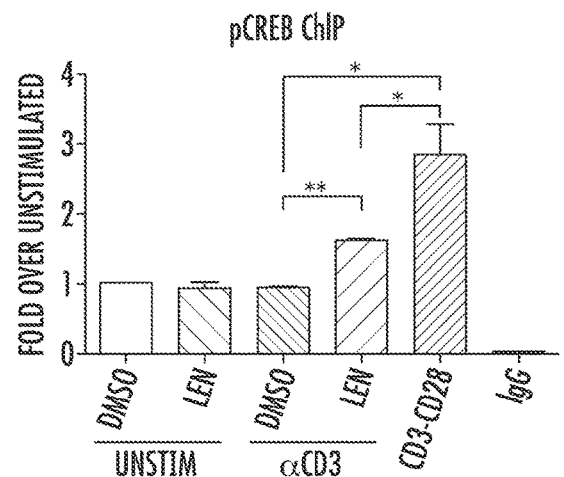
FIG. 2B shows pCREB binding to the IL-2 promoter after 18 hours stimulation with 1.0 μm/ml anti-CD3 antibody in the presence of vehicle (DMSO) or 10 μM Len treatment. CD3$^+$CD28 stimulation and IgG pull-down were used as positive and negative controls, respectively. All values were calibrated to 10% input and calculated using ΔΔCT method relative to un-stimulated treated with DMSO. Graph is representative of 2 replicates. Statistical analysis was performed using an unpaired T-test. *$p<0.05$ **$p<0.01$.

Since LEN increases IL-2 gene expression, likely through the CD28 pathway, it was determined if LEN augments the binding of a CD28-specific transcription factor to the IL-2 promoter in primary human T-cells. Multiple transcription factors are required to interact with the IL-2 promoter for transcriptional initiation (FIG. 2A). Some transcription factors are regulated by the TCR signaling cascade, such as NFAT-1, AP-1, and NF-κB, but binding by these factors alone is insufficient for IL-2 gene transcriptional activation (Kane L P, et al. Trends Immunol 2002 23(8):413-20). Only binding of transcription factors such as pCREB (a CD28-Response Element specific binding factor), NF-κB and AP-1 within the CD28 response element following CD28 receptor ligation is capable of inducing IL-2 transcription. To determine if LEN treatment induces the binding of pCREB to the IL-2 promoter in the absence of CD28 co-ligation, chromatin immunoprecipitation was performed (FIG. 2A). Results shown in FIG. 2B shows that with anti-CD3 treatment alone, LEN increases binding of pCREB to the IL-2 promoter compared to DMSO and indicates that LEN induces the CD28 pathway in conjunction with TCR stimulation.

Surface Expression of CD28 is Increased after LEN Treatment Upon TCR Activation.

Figure 3A:
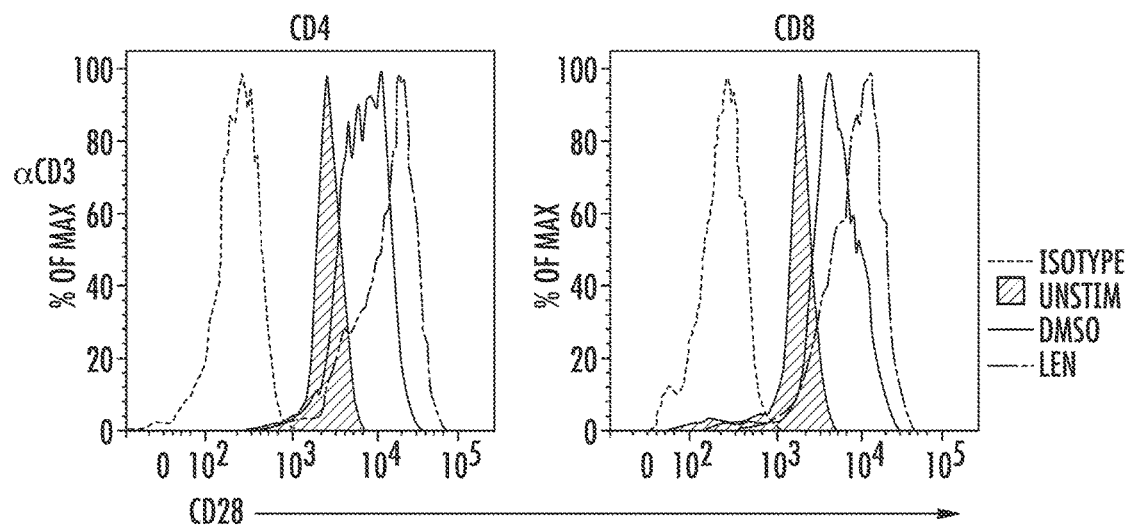
FIG. 3 shows surface expression of CD28 is increased after LEN treatment upon TCR activation. Isolated T-cells were treated with Len or DMSO and stimulated with polystyrene beads coated with anti-CD3 antibody alone. CD28 surface expression was measured 3 days after stimulation by flow cytometry, and an example histogram of CD28 surface expression after anti-CD3 stimulation is shown in (FIG. 3A). The black line indicates PE-isotype (negative control), red shaded region represents un-stimulated T-cells, blue line represents DMSO treated, and green line is LEN treated T-cells.
FIG. 3B is a graph showing the CD28 MFI in one of four independent experiments on both CD4$^+$ (left) and CD8$^+$ (right) T-cells.
FIG. 3C shows mRNA expression of CD28 and FIG. 3D shows Western blot analysis for CD28 expression after T-cells were treated with 10 ug/ml of anti-CD3 and 2.0 μg/ml of anti-CD28 for 1, 2 4, 8 12, and 48 hours. Blotting with anti-β-actin confirmed equal protein loading. The difference between LEN and DMSO was determined using 2-way non-parametric ANOVA =$p<0.01$, *=$p<0.001$.
Figure 3B:
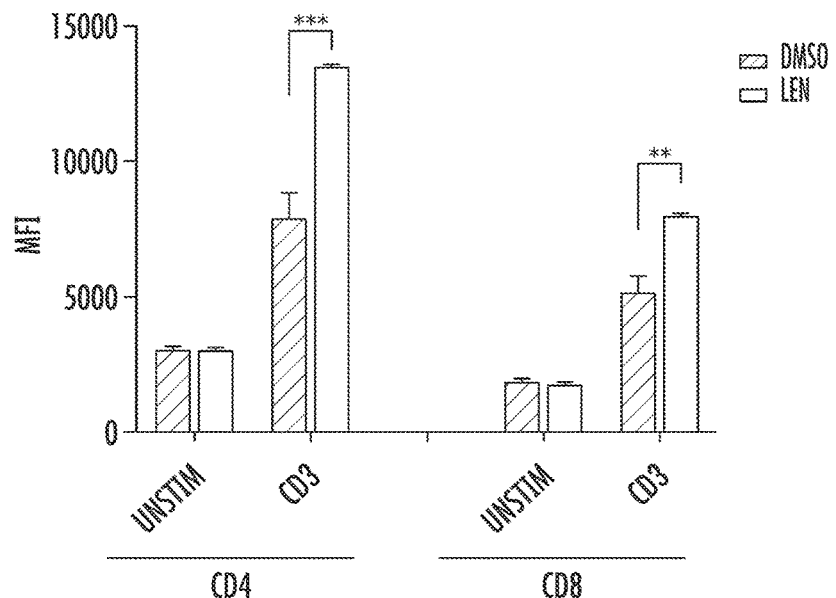
Figure 3C:
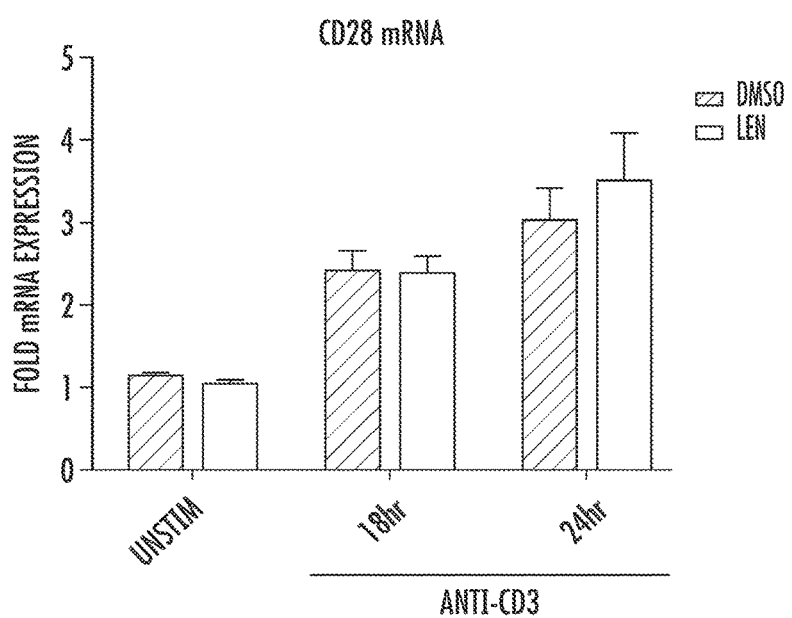
Figure 3D:
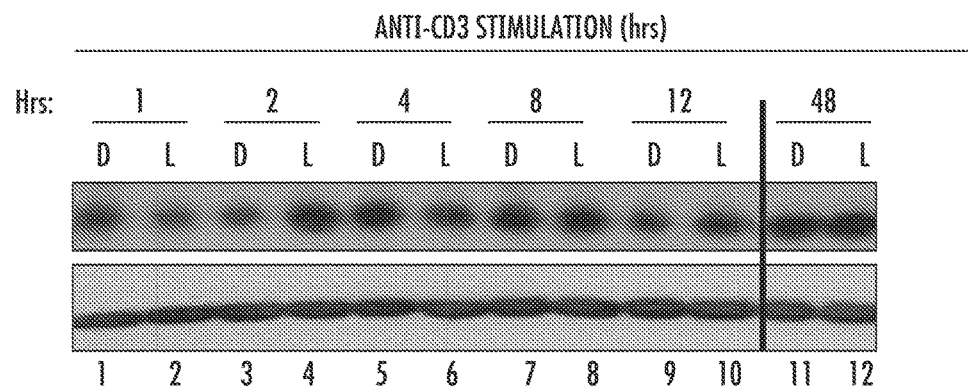

Since LEN augments T-cell function through the CD28 pathway, it is possible that LEN alters CD28 surface expression. The surface expression of CD28 was therefore examined in primary T-cells from healthy donors that were either left un-stimulated or stimulated with anti-CD3 for 72 hours (FIG. 3). FIG. 3A shows a representative flow plot of CD28 surface expression under these conditions. Treatment of cells with anti-CD3 alone in the absence of CD28 co-ligation results in a significant increase in the number of CD28 molecules per cell compared to unstimulated cells, as indicated by a shift in median fluorescence intensity (MFI). LEN amplifies this anti-CD3 response compared to DMSO-treated cells (FIG. 3A-B). Elevated transcription of CD28 mRNA (FIG. 3C) is at least partially responsible for CD28 induction after TCR stimulation. However, LEN did not significantly increase either CD28 mRNA after 18 or 24 hours (FIG. 3C) or total protein expression of CD28 compared to anti-CD3 activation for 1, 2, 4, 8, 12, and 48 hours (FIG. 3D) suggesting that the drug may increase CD28 expression by modulating intracellular trafficking.

CD28 Surface Expression is Essential for LEN-Induced IL-2 Production.

Figure 4A:
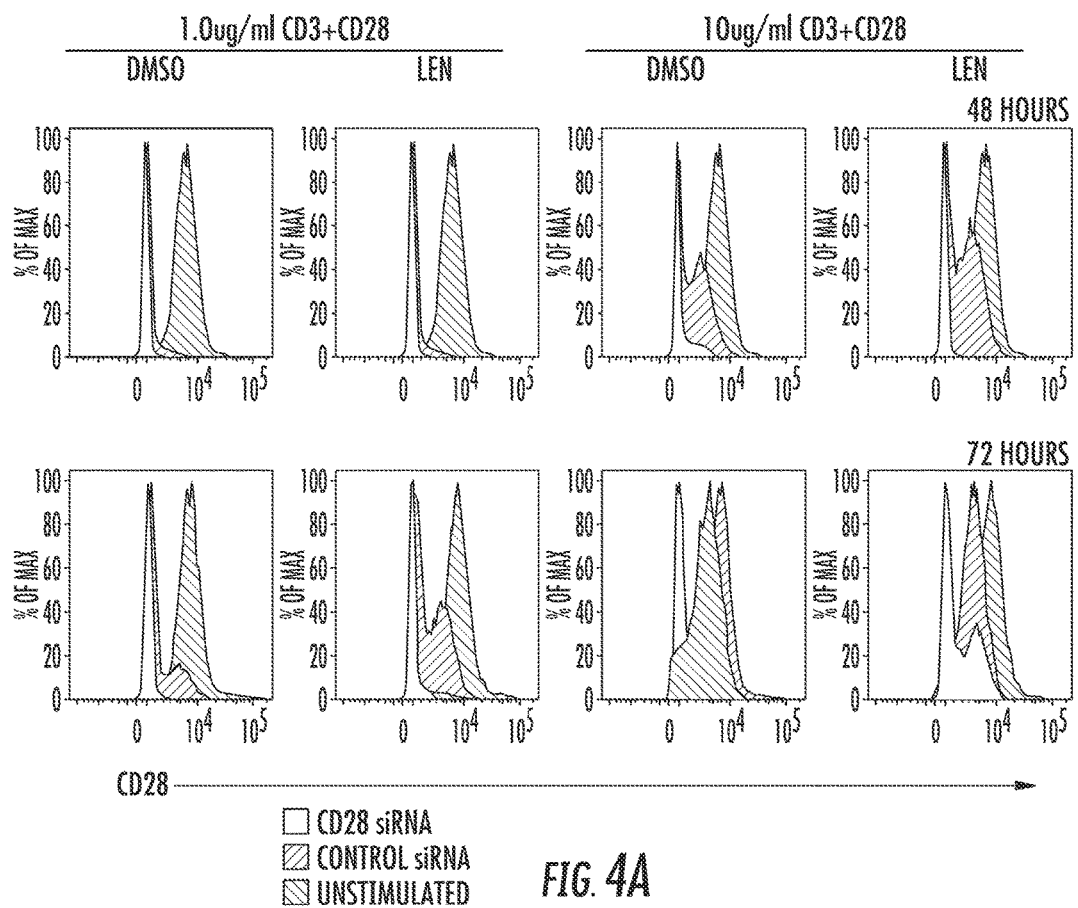
FIG. 4A shows examples of flow cytometry plots of one experiment to evaluate CD28 expression after siRNA infection and plate bound stimulation at 48 and 72 hour time points. Un-stimulated T-cells were used as positive control for CD28 expression.
Figure 4B:
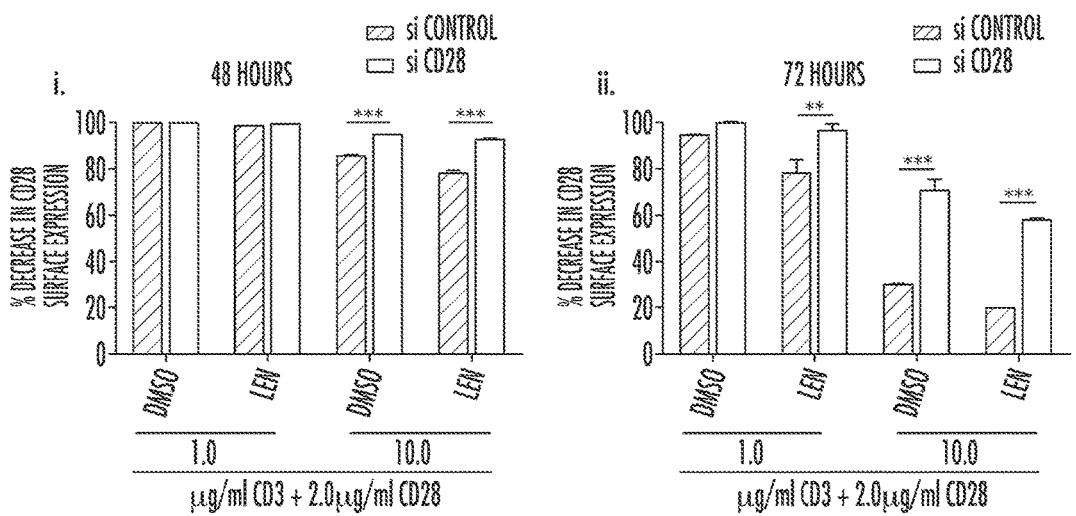
FIGS. 4B(i) and 4b(ii) are bar graphs that quantitatively represent the average % decrease in CD28$^+$ T-cells at 48 and 72 hours from 3 independent experiments.

To elucidate whether surface CD28 receptor expression is necessary for LEN-induced IL-2 production, $CD28^+$ T-cells were purified by flow cytometry sorting and then subjected to either CD28 siRNA or control siRNA treatment. Reduction in CD28 expression in primary T-cells utilizing siRNA technology is complicated by the long protein half-life and stable cell surface expression of CD28 in the absence of ligation. Engagement of the extracellular portion of the CD28 receptor with anti-CD28 antibody cross-linking transiently induces its internalization (Cefai D, et al. J Immunol 1998 160(5):2223-30). Some CD28 is then targeted for degradation in the endosome while most is recycled back to the surface. As shown in FIG. 4A, surface expression of CD28 was reduced by treating with varying doses of anti-CD3 in combination with anti-CD28 antibodies to induce receptor internalization. An example of the surface expression of CD28 by flow cytometry in the knockdown experiments is also shown in FIG. 4A, and quantified in FIG. 4B. Flow cytometry confirmed that CD28 expression, in the presence or absence of LEN, was significantly reduced after co-stimulation, with the rate and degree of surface recycling depending on the TCR signal strength indicating that LEN does not impair ligand-induced internalization. It was evident that 10 µg/ml of anti-CD3 significantly increased the rate (24 versus 48 hours) and proportion of cells that re-express CD28 (FIG. 4A). Although internalization was unaffected, re-expression was slightly increased by LEN in this experiment. siRNA-treated cells were compared to siRNA control (FIG. 4)-treated cells after 24 and 48 hours in the presence of 1.0 or 10 µg/ml of anti-CD3 plus anti-CD28 antibody stimulation. Compared to control siRNA, siRNA-CD28 treatment significantly reduced the expression of CD28 in all conditions.

Figure 4C:
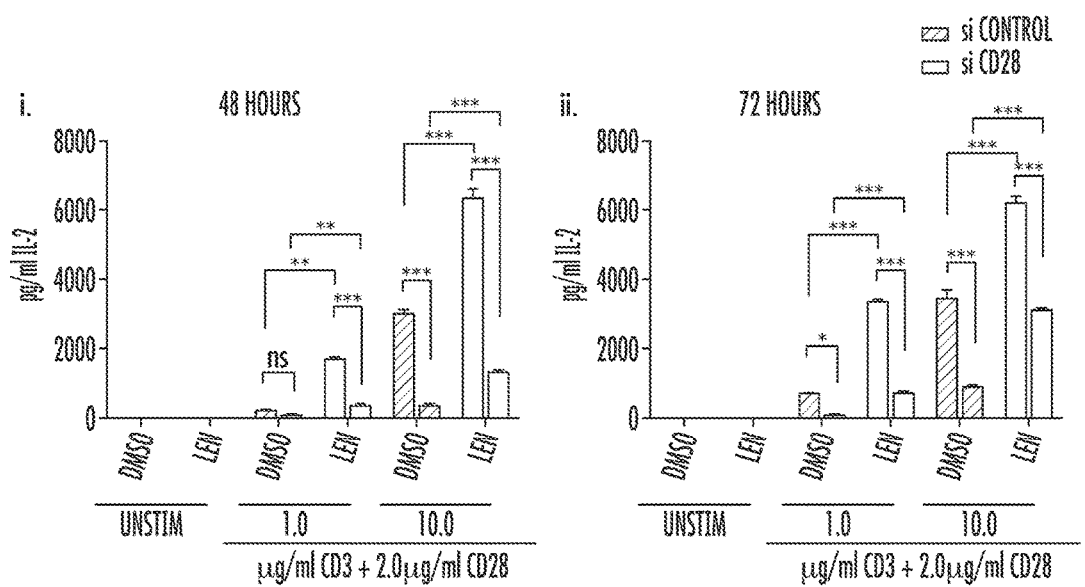
FIGS. 4C(i) and 4C(ii) are bar graphs showing IL-2 secretion in the supernatant in cells from A-B collected after 48 and 72 hours of stimulation and evaluated by ELISA. Statistical analysis was performed using 2-Way ANOVA. $P<0.001$ *$P<0.001$.

Production of IL-2 in LEN or DMSO-treated cells with either siRNA-CD28 knockdown or control siRNA is shown in FIG. 4C. Reduction in CD28 significantly diminished IL-2 and effectively blocked LEN-induced IL-2 release (decreased from a 7.5-fold increase to 4.9-fold increase on average compared to control siRNA), as shown in FIG. 4C. This data suggests that the expression of CD28 on the surface imparts responsiveness to LEN.

CD28-T-Cells are Resistant to LEN.

Figure 5A:
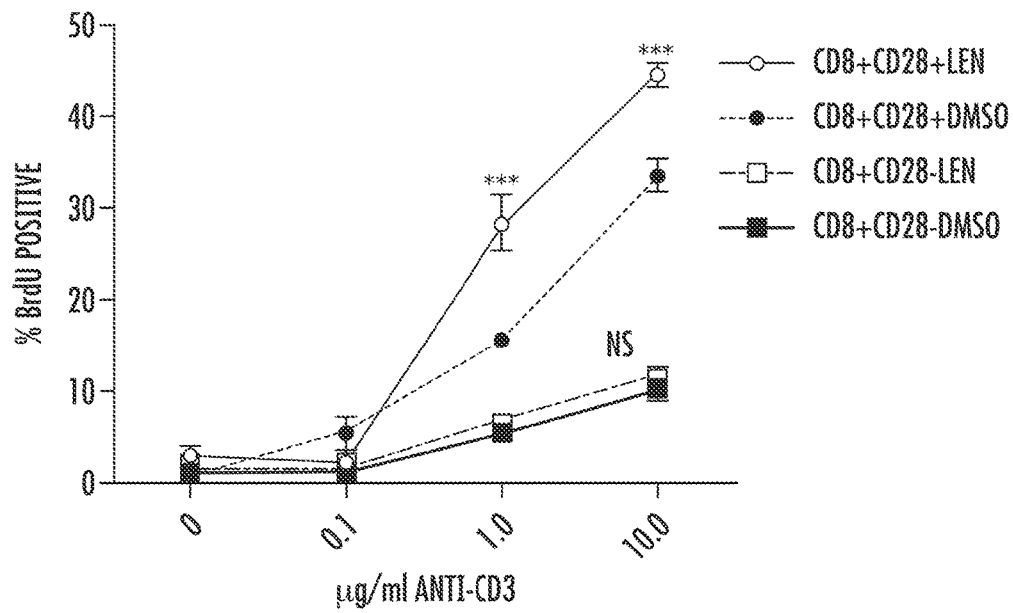
In FIG. 5A, BrdU incorporation was used to measure proliferation of sorted CD8$^+$CD28$^+$ and CD8$^+$CD28$^-$ T-cells as determined via flow cytometry on day 3.
Figure 5B:
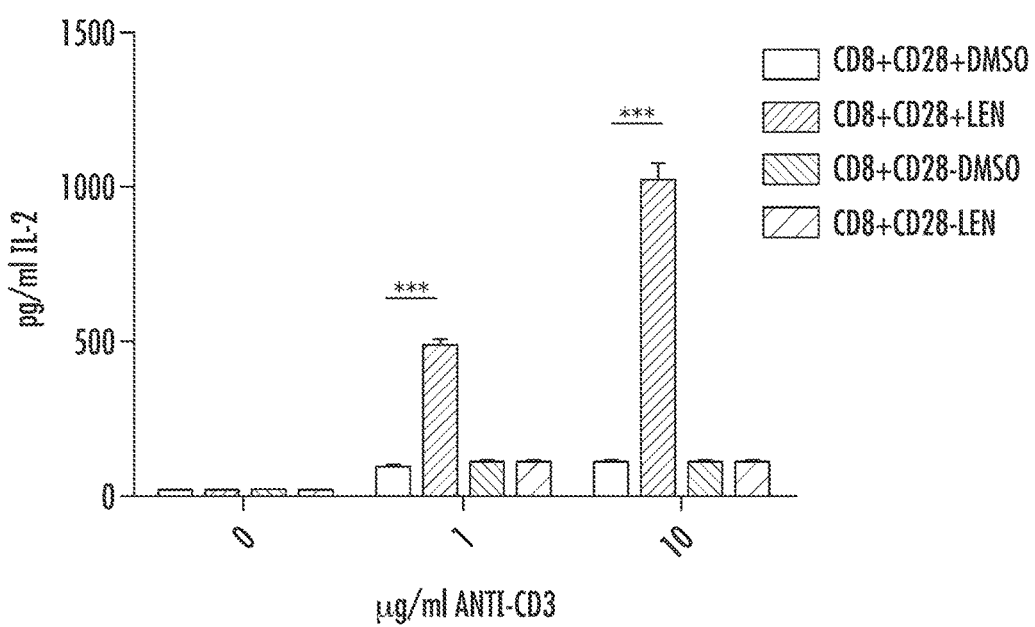
In FIG. 5B, CD8$^+$CD28$^+$, CD8$^+$CD28$^-$ T-cells were stimulated, and supernatant was collected on day 3 of stimulation. IL-2 secretion was measured via ELISA. *** $p<0.001$. MDS patient PBMCs prior to lenalidomide treatment were analyzed for CD28 expression, and correlated with hematologic response.

CD28 surface expression is lost on $CD8^+$ memory T-cells as a function of aging, which contributes to the accumulation of $CD8^+CD28^-$ T-cells (Czesnikiewicz-Guzik M, et al. Clin Immunol 2008 127(1):107-18). The loss of CD28 expression is unique to the CD8 compartment in humans, as there is little or no accumulation of $CD28^-$ murine T-cells or $CD4^+CD28^-$ T-cells in healthy individuals (Effros R B. Dev Comp Immunol 1997 21(6):471-8). It was then determined if LEN co-stimulates naturally occurring $CD28^-$ T-cells. Sorted was done on $CD8^+CD28^+$ and $CD8^+CD28^-$ T-cells from healthy donors, the cells stimulated ex-vivo with anti-CD3 and proliferation and IL-2 production examined from these two distinct T-cell subsets (FIG. 5A-B). As shown in FIG. 5A, LEN increased proliferation of $CD8^+CD28^+$ T-cells in a dose-dependent fashion with anti-CD3 stimulation alone. The $CD8^+CD28^-$ T-cell population displayed an overall significant reduction in proliferation compared to the $CD28^+$ T-cells, and displayed no response to LEN compared to DMSO-treated cells after anti-CD3 stimulation (FIG. 5A). Elaboration of IL-2 was also completely abolished in $CD8^+CD28^-$ T-cells with no response to LEN. These results indicate that the surface expression of CD28 on T-cells is indispensable for LEN immunomodulatory response and that the drug cannot overcome signaling dysfunction that occurs in $CD28^-$ cells.

Accumulation of $CD28^-$ T-cells in MDS patients is associated with LEN failure.

Figure 5C:
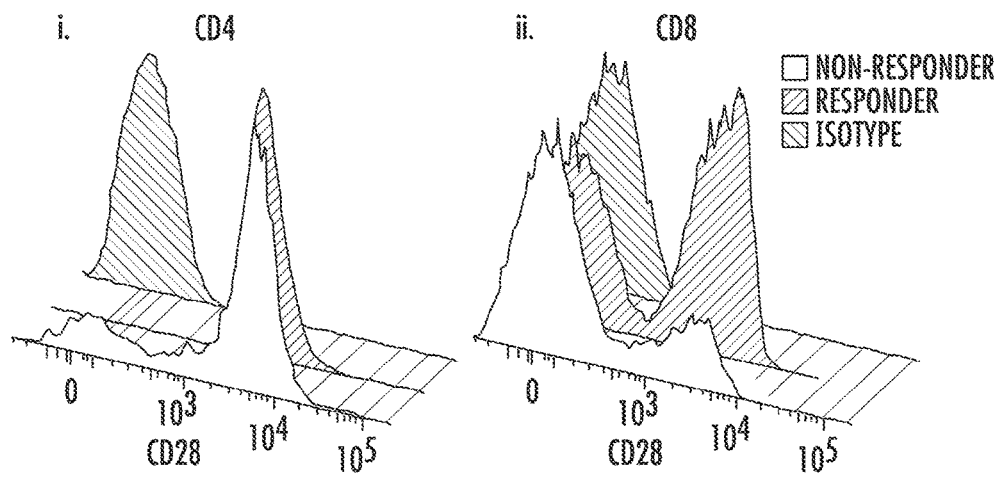
FIGS. 5C(i) and 5C(ii) are representative histograms of CD28 expression on both CD4$^+$ (5C(i)) and CD8$^+$ (5C(ii)) T-cells of erythroid Non-Responders (NR) and Responders (R). Percentage of CD28$^+$ T-cells from both CD4$^+$ (FIG. 5D) and CD8$^+$ (FIG. 5E) populations was analyzed in 7 NR and 4R. The difference between the two groups was determined using a Mann-Whitney T-test with p-values indicated on graphs.
Figure 5D:
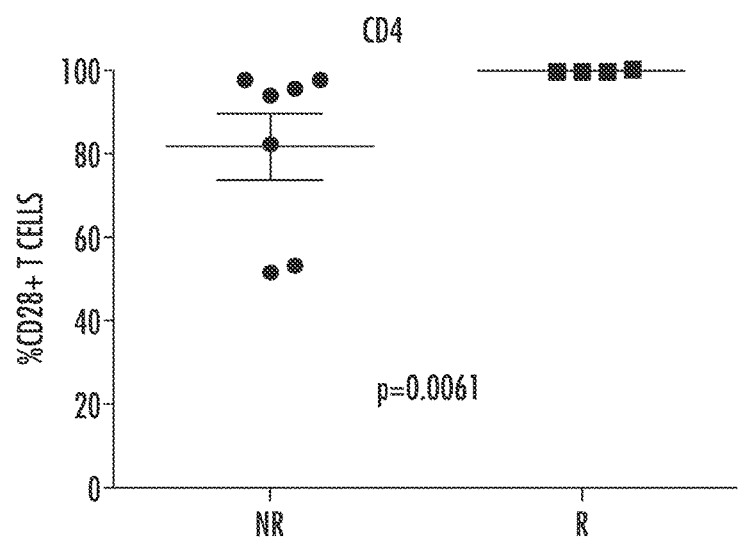
FIG. 5 shows CD28$^+$ T-cells are associated with LEN Response. A-B. Healthy donor CD8 T-cells were sorted into CD28$^+$ and CD28$^-$ populations before being stimulated for 3 days in the presence of increasing concentrations of plate bound anti-CD3 antibody (μg/ml) in the presence of DMSO (Vehicle) or 10 μM Lenalidomide.
Figure 5E:
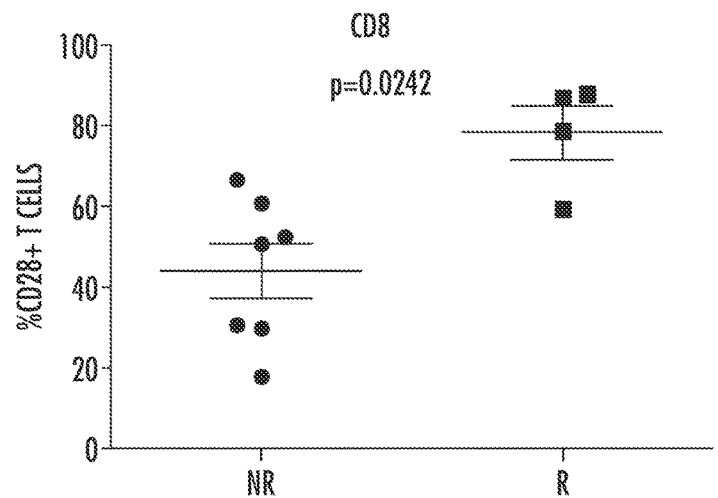

Although LEN is approved for the treatment of MDS and MM, there are subsets of patients that are naturally resistant to the drug. Since CD28 expression is essential for LEN immunomodulatory effects in T-cells, CD28 expression was analyzed on T-cells from MDS patients in relationship to hematologic response (FIG. 5C-E). Blood was taken from patients prior to LEN treatment, and the percentage of CD28 positive cells was compared in responders (R) and non-responders (NR). Hematologic response was assessed after 16 weeks of treatment using IWG criteria for hematologic improvement. As shown in a representative R and NR patient (FIG. 5C), the percentage of $CD28^+$ cells was greater in the R compared to the NR. Data on this subgroup of MDS patients (FIG. 5D) indicate that the proportion of CD28 expressing cells prior to LEN treatment is significantly associated with clinical outcome favoring more $CD28^+$ cells in the responders. Although CD4 T-cells rarely lose CD28 expression in healthy donors, the NR MDS cohort had a significant accumulation in $CD4^+ CD28^-$ T-cells (p=0.0061 FIG. 5D). A similar significant decrease in the percentage of $CD28^+$ T-cells in NR patients was also seen in the CD8 compartment (p=0.0242) (FIG. 5E). This data shows a correlation between accumulation of $CD28^-$ T-cells and resistance to LEN in MDS.

Figure 6A:
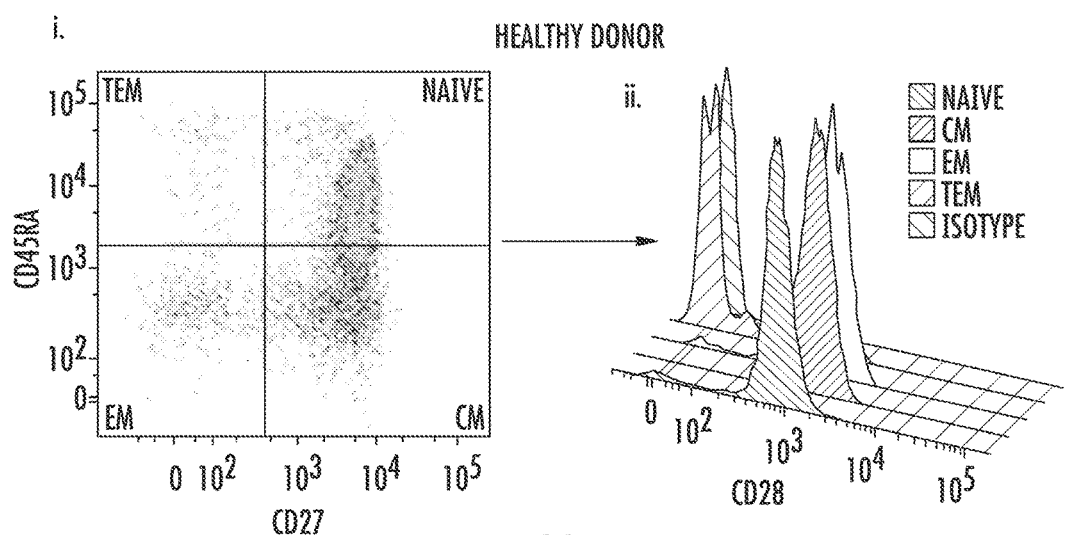
FIGS. 6A-6C show phenotypes of CD3$^+$ Healthy Donor (FIG. 6A) and MDS patients (FIG. 6B, Responders, R) and (FIG. 6C, Non-Responders, NR) and CD28 expression within each memory subset.
Figure 6B:
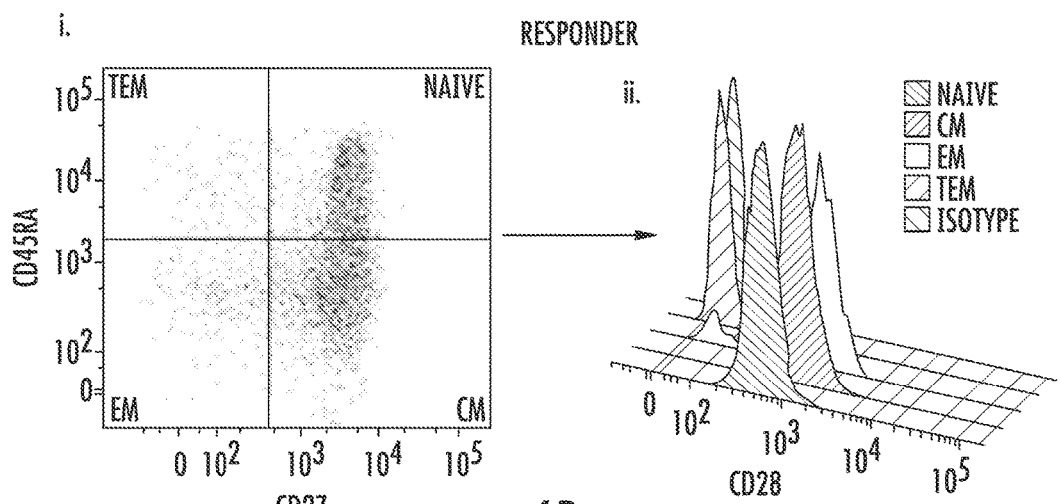
Figure 6C:
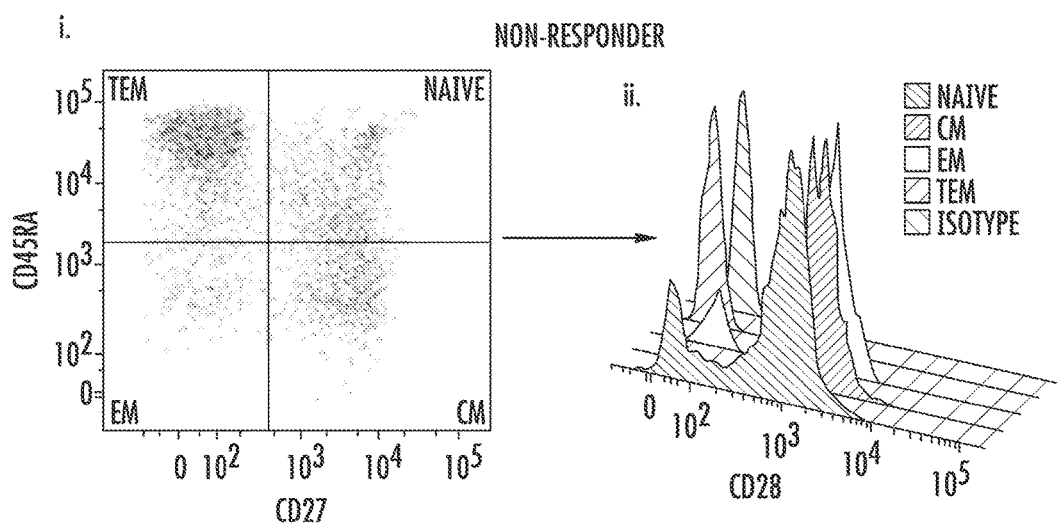
Figure 6D:
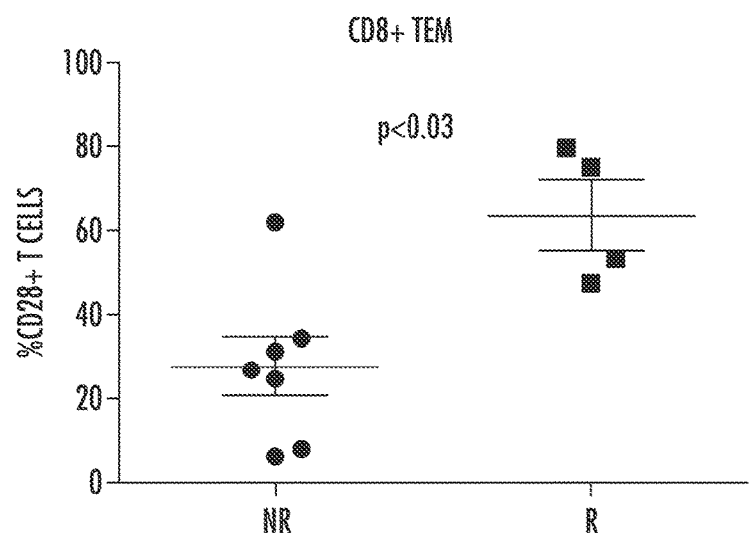
FIG. 6D shows quantification of CD28$^+$ T-cells within the TEM compartment in LEN-treated NR (n=7) and R (n=4) MDS patients.
Figure 6E:
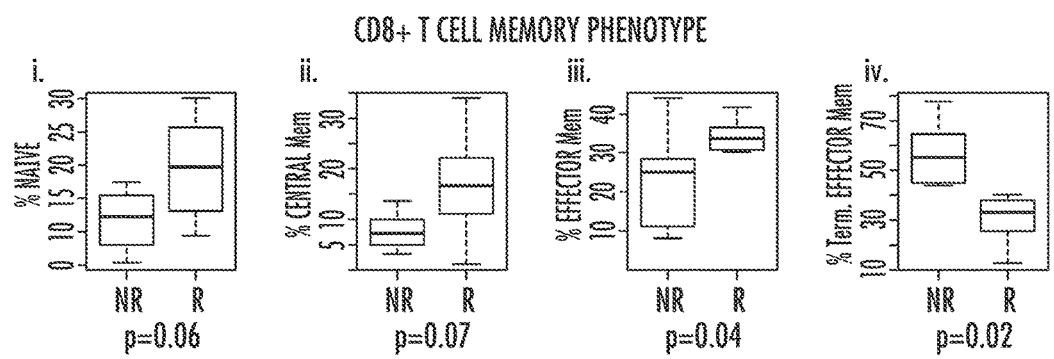
FIG. 6E shows the proportion of each memory phenotype making up the CD8 T-cell compartment is shown for both Responding (R) and Non-Responding (NR) patients prior to LEN treatment, and is correlated with response after 16 weeks of in vivo treatment. Statistical analysis was performed using Wilcoxon Rank Sum Test.
Figure 6F:
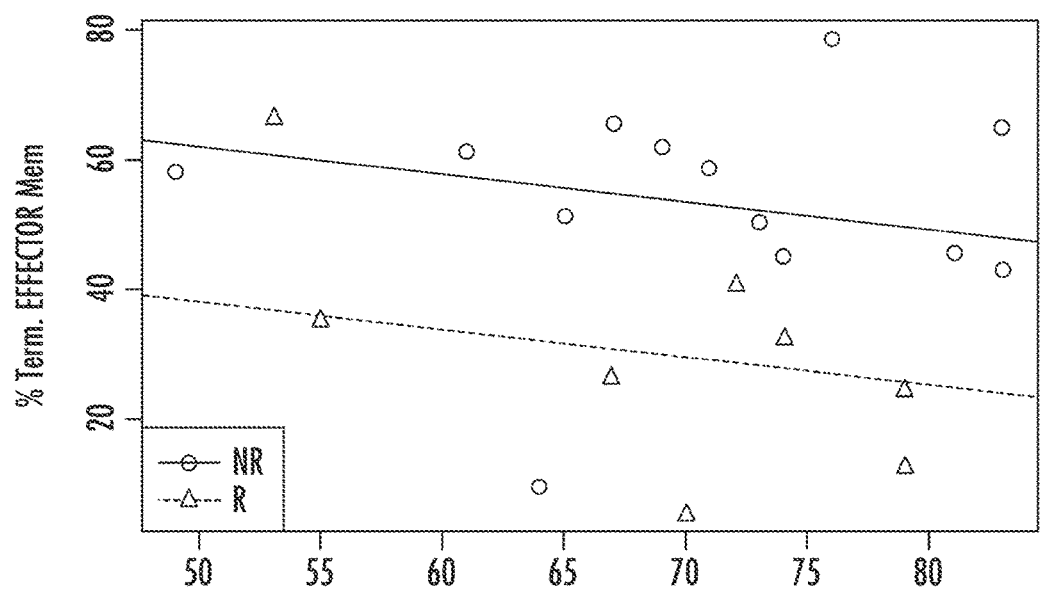
FIG. 6F shows the proportion of CD8$^+$ TEM cells compared with age in MDS Responder (R) and Non-Responder (NR) patients (p=ns).

MDS patients who respond to LEN therapy have significant changes in the naive and memory T-cell compartment after LEN treatment (McDaniel J M, et al. Leukemia 2012 26(6):1425-9). Cells with a $CD28^-$ phenotype generally express CD45RA but lack lymphoid-homing receptors such as CCR7, CD62L, and CD27, and these terminal effector memory (TEM) cells increase with age and are associated with autoimmunity (Schmidt D, et al. J Clin Invest 1996 97(9):2027-37). The pre-treatment percentage of $CD8^+$ naïve and memory T-cells (central memory, effector memory, and TEM cells) was then compared in LEN-treated MDS patients and correlated with response (R verses NR). FIG. 6A-C are representative flow plots of CD28 expression in the different memory phenotypes on T-cells from a healthy donor (FIG. 6A), Responder (FIG. 6B), and Non-Responder (FIG. 6C). There was a clear distinction in the T-cell phenotype based on hematologic response. $CD8^+$ TEM cells were significantly expanded in NR compared to R (p=0.02) (FIG. 6E), where both naïve and central memory T-cells showed a tendency toward lower percentages (p=0.06 and =p=0.07). The difference in TEM $CD8^+$ T-cells also reflects the reduction in the percentage of TEM expressing CD28 (FIG. 6D, p=0.03). Although $CD28-CD8^+$ TEM T-cells accumulate with age, the increase in these cells in NR was not associated significantly with age, as shown in FIG. 6F. These results indicate that CD28 expression is necessary for immunologic responsiveness to LEN and loss of CD28 expression of $CD8^+$ and $CD4^+$ T-cells correlates with resistance to LEN in MDS.

DISCUSSION

LEN is a highly potent immunomodulatory drug (IMID®) used to potentiate T-cell and NK cells in a number of hematologic and solid malignancies. CD28 ligation with CD80/CD86 on APCs in the presence of anti-TCR ligation enables a fully competent signal response by T-cells, inducing cytokine production and proliferation, and preventing anergy (Linsley P S, et al. Immunity 1994 1(9):793-801). Anergy induction and T-cell non-responsiveness to tumor antigens are major obstacles to tumor immunotherapy. In solid tumors and hematologic malignancies, there is little expression of co-stimulatory molecules on the tumor cells themselves, as well as down-regulation of co-stimulatory molecules on DCs within the tumor environment (Brown R D, et al. Blood 2001 98(10):2992-8). The lack of co-stimulation induces tolerance or ignorance by the immune system, preventing tumor-cell detection and eradication. LEN is being investigated as a single agent or in combination regimens in a number of solid and hematologic malignancies (Galustian C, et al. Cancer Immunol Immunother 2009 58(7):1033-45; Giannopoulos K, et al. Leukemia 2008 22(1):222-4). LEN's successes in hematologic malignancies like B-Chronic Lymphocytic Leukemia (B-CLL) (Giannopoulos K, et al. Leukemia 2008 22(1):222-4), Non-Hodgkin's Lymphoma (NHL) (Fowler, et al. J Clin Oncol 2009 27(15s):8548) and MM (Noonan K, et al. Clin Cancer Res 2012 18(5):1426-34) is attributed to amplification of $CD8^+$ tumor-specific T-cells or NK cells, as well as direct antitumor activity. Clinical studies in solid malignancies such as melanoma and ovarian cancer have not demonstrated single-agent activity and only nominal survival benefit (Eisen T, et al. Cancer 2010 116(1):146-54; Glaspy J, et al. Cancer 2009 115(22):5228-36; Zhang M M, et al. Gynecol Oncol 2007 105(1):194-8). The combination of LEN with chemotherapy, however, has shown greater activity. For immunotherapy, benefit of the drug is evident in several solid tumor settings including metastatic melanoma (Hwu W J, et al. Melanoma Res 2010 20(6):501-6), castration resistant prostate cancer (Petrylak D P, et al. ASCO annual meeting, Journal of Clinical Oncology 2009), pancreatic adenocarcinoma (Arkenau H, et al. Journal of Clinical Oncology 2011; 29), and ovarian cancer (Carter J S, et al. Int J Clin Oncol 2011 16(6):666-70). The disclosed data indicates that the drug may overcome lack of co-stimulation if CD28 is expressed on T-cells.

LEN augments the production of IL-2 in the presence of anti-TCR activation alone (FIG. 1) in purified human CD4 and CD8 T-cells, a function that is closely tied to CD28 signaling. Although LEN may replace the need for external ligation of this co-stimulatory molecule, the requirement for, and the effect of LEN on CD28 surface expression is disclosed. It is likely that receptor expression is necessary as it acts as a scaffold at the immune synapse for the recruitment of signaling molecules leading to IL-2 expression and proliferation (Salmond R J, et al. Immunol Rev 2009 228 (1):9-22). pCREB binding to the CD28-Response Element on the IL-2 promoter further supports this idea. The role of CD28 in LEN immune activation would be ideally determined using T-cells from CD28 knockout mice as these mice lack IL-2 transcriptional activation (Sanchez-Lockhart M, et al. J Immunol 2004 173(12):7120-4; Shahinian A, et al. Science 1993 261(5121):609-12). Due to accelerated drug metabolism, altered pharmacokinetics, or differential molecular regulation within the CD28 signaling pathway in murine T-cells, it is disclosed that immune modulation by LEN is species specific (FIG. 1).

To evaluate the role of CD28 in human T-cells, a knock-down approach was used along with evaluation of naturally-occurring CD28 deficient cells. The disclosed data reveal a new aspect of LEN function and implicates CD28 receptor in the molecular mechanism. Thalidomide was shown to induce teratogenicity by directly interacting with cereblon (CRBN) in chicken and zebrafish embryos (Ito T, et al. Science 2010 327(5971):1345-50). CRBN was discovered in the brain where it regulates behavior and cognition (Rajadhyaksha A M, et al. Behav Brain Res 2012 226(2): 428-34) and it acts as an E3 ubiquitin ligase when complexed with damaged DNA binding protein 1 (DDB1) and Cu14A (Angers S, et al. Nature 2006 443(7111):590-3). A direct interaction between thalidomide and CRBN blocked the ternary complex's ability to execute E3-ubiquitin ligase function (Ito T, et al. Science 2010 327(5971):1345-50). The T-cell stimulatory activity of LEN and the thalidomide analog pomalidomide is reduced after knockdown of CRBN (Lopez-Girona A, et al. Leukemia 2012) suggesting that it is involved in immune modulation.

For T-cell regulation, other E3 Ub ligases, like Casitas-B-lineage lymphoma protein-b (Cbl-b) and ITCH play a major role in T-cell anergy through ubiquitination of CD28 targets (Venuprasad K. Cancer Res 2010 70(8):3009-12). In the absence of CD28 stimulation, monoubiquitination represses the trafficking of signaling molecules, such as TCRζ, to the signaling complex thus setting the threshold for T-cell activation by blocking PI3K and Vav1 activation. Ligation of CD28 receptor by B7-1/2 or antibody crosslinking overcomes this repression by activating PLC-γ and PKC-θ, which in turn targets Cbl-b for degradation (Gruber T, et al. Sci Signal 2009 2(76):ra30). Cbl-b homozygous deficient mice exhibit lipid raft aggregation, sustained tyrosine phosphorylation of Vav1 and IL-2 production in response to anti-CD3 stimulation without CD28 ligation, similar to LEN treatment (Bachmaier K, et al. Nature 2000 403(6766):211-6; Chiang Y J, et al. Nature 2000 403(6766): 216-20). Cbl-b deficiency leads to spontaneous autoimmune-mediated diabetes, increased susceptibility to experimental autoimmune encephalomyelitis (Bachmaier K, et al. Nature 2000 403(6766):211-6; Chiang Y J, et al. Nature 2000 403(6766):216-20), which is a mouse model of multiple sclerosis, and Cbl-b-null T-cells mediate more efficacious responses to tumors (Schmitz M L. Sci Signal 2009 2(76):pe38). Whether LEN can target other E3 Ub ligases, such as Cbl-b or ITCH, or whether CRBN plays an undefined role in regulating CD28 signaling remains to be determined. It is evident from the disclosed results, however, that LEN does not interfere with CD28 receptor internalization and acts to stimulate receptor recycling.

Although LEN is an efficacious drug in MDS and hematologic malignancies, and has shown potential in a variety of solid tumors, there are still subsets of patients that fail to respond. Therefore, pre-treatment predictive biomarkers may assist with patient selection. It is disclosed that CD28 on T-cells is an indicator of LEN immune modulating potential (FIG. 4) and that hematologic response to LEN in MDS involves the immune response (McDaniel J M, et al. Leukemia 2012 26(6):1425-9; Noonan K, et al. Clin Cancer Res 2012 18(5):1426-34). The disclosed data indicates that the accumulation of $CD28^-$ T-cells can be a factor in LEN resistance.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject with myelodysplastic syndrome (MDS), comprising:
   a) assaying a sample from the subject for surface expression of CD28 on $CD4^+$ and/or $CD8^+$ T-cells; and
   b) treating the subject with lenalidomide if elevated numbers of $CD8^+$ T-cells in the sample have detectable CD28 surface expression compared to a lenalidomide non-responder control, elevated numbers of $CD4^+$ T-cells in the sample have detectable CD28 surface expression compared to a lenalidomide non-responder control, or a combination thereof.

2. The method of claim 1, comprising treating the subject with lenalidomide if elevated numbers of $CD8^+$ T-cells in the sample have detectable CD28 surface expression compared to a lenalidomide non-responder control.

3. The method of claim 1, comprising treating the subject with lenalidomide if elevated numbers of $CD4^+$ T-cells in the sample have detectable CD28 surface expression compared to a lenalidomide non-responder control.

4. The method of claim 1, wherein the myelodysplastic syndrome is a non-del(5q) MDS.

5. The method of claim 1, wherein the subject is co-administered lenalidomide with another chemotherapeutic.

6. The method of claim 1, wherein the surface expression of CD28 is detected by flow cytometry.

* * * * *